| United States Patent [19] | [11] Patent Number: 4,992,479 |
|---|---|
| Van Dijk et al. | [45] Date of Patent: Feb. 12, 1991 |

[54] PROCESS FOR THE PREPARATION OF METHANOL AND COMPOSITION SUITABLE FOR USE AS A CATALYST IN SAID PROCESS

[75] Inventors: Arjan Van Dijk; Eit Drent; Andras G. T. G. Kortbeek, all of Amsterdam, Netherlands

[73] Assignee: Shell Oil Company, Houston, Tex.

[21] Appl. No.: 426,643

[22] Filed: Oct. 26, 1989

[30] Foreign Application Priority Data

Nov. 1, 1988 [GB] United Kingdom ................. 8825516

[51] Int. Cl.$^5$ ............................................. C07C 27/26
[52] U.S. Cl. .................................. 518/700; 518/713; 502/186
[58] Field of Search ......................................... 518/700

[56] References Cited

U.S. PATENT DOCUMENTS 4,614,749  9/1986  Saprenza et al. ................... 518/700
4,619,946 10/1986  Saprenza et al. ................... 518/700

FOREIGN PATENT DOCUMENTS 6169634   3/1980  Japan .
56-110631  4/1980  Japan .
6110631   4/1980  Japan .
110631    9/1981  Japan .
169634   12/1981  Japan .

Primary Examiner—Howard T. Mars

[57] ABSTRACT

Process for the preparation of methanol by contacting a gaseous mixture comprising carbon monoxide and hydrogen with a novel catalytic system formed by combining (a) a copper salt (b) an alcohol, and (c) a complex hydride, and allowing the combined components to react.

12 Claims, No Drawings

PROCESS FOR THE PREPARATION OF METHANOL AND COMPOSITION SUITABLE FOR USE AS A CATALYST IN SAID PROCESS

FIELD OF THE INVENTION

The invention relates to a process for the preparation of methanol from a gaseous mixture comprising carbon monoxide and hydrogen and to a catalyst composition suitable for use in said process.

BACKGROUND OF THE INVENTION

A process for the preparation of methanol is described in U.S. Pat. No. 4,619,946 comprising reacting carbon monoxide and hydrogen at relatively low temperature in the presence of a catalytic system derived from sodium hydride, a sodium alcoholate and an acetate of nickel, palladium or cobalt. The alcoholate applied is preferably a lower alkanolate having 1-6 carbon atoms. As metal salt nickel acetate is preferably used. The catalyst is subjected to a conditioning or activating step for a prolonged time with a gaseous mixture comprising carbon monoxide and hydrogen at such an elevated temperature and elevated pressure that a substantial amount of carbon monoxide and hydrogen is consumed for this conditioning.

In U.S. Pat. No. 4,614,749 a process is disclosed for the preparation of methanol by reaction of carbon monoxide and hydrogen in the presence of a slurry catalyst system resulting from combination of (1) a reducing agent comprising sodium hydride-alcohol and an acetate of nickel, palladium or cobalt, and (2) a carbonyl complex of one of the group VI metals.

Another process for the preparation of methanol is described in Japanese Patent No. 56-169,634. This process comprises reacting carbon monoxide and hydrogen in the presence of a catalyst comprising a nickel compound and a metal alkoxide. The catalyst to be used for this process may be prepared by mixing a nickel compound with an alkali metal alkoxide. It is preferred to use a liquid organic diluent. It is observed that this Japanese application teaches a person skilled in the art, that a high reaction rate may be reached by preparing the catalyst system with the use of a substantially alcohol free organic diluent and that it is desirable that an alcohol be not present in the reaction system at the commencement of the reaction. Moreover from this Japanese patent application and especially from its example 2, it clearly appears that at low temperature only small amounts of methanol are produced in favour of production of methyl formate in large amounts.

In Japanese Patent No. 56-110631 a process is described for the preparation of methanol comprising the use of a catalytic system derived from a hydride, an alcoholate and a copper salt. Relatively high reaction temperatures and pressures are necessary in order to obtain a reasonable yield of methanol.

Although improvements in the performances of the catalyst systems as described hereinbefore, could be reached as compared to those used in the conventional methanol manufacturing processes, requiring severe conditions, the still growing demand for cheaper methanol as starting material for a still increasing area of chemical syntheses evoked continuing research efforts for a further improved methanol manufacturing process as compared to the currently operated high pressure processes.

With the term improved methanol manufacturing process is meant a process utilizing a catalyst having enhanced activity at low temperatures, and retaining its activity for a long time under economically more attractive operating conditions.

An object of the present invention is therefore to provide such an improved manufacturing process for methanol, as well as to provide an improved catalytic system therefor.

SUMMARY OF THE INVENTION

The instant process comprises contacting a gaseous mixture comprising carbon monoxide and hydrogen with a catalytic system obtainable by combination of:
component (a): a copper salt,
component (b): an alcohol, and
component (c): a complex hydride,
and allowing the combined components to react.

DETAILED DESCRIPTION OF THE INVENTION

The anion of the salt in component (a) may be derived from a great variety of acids. It is preferred that the salt in component (a) is a salt of a carboxylic acid or sulphonic acid. Among these acids preference is given to alkanoic acids having 1-10 carbon atoms in the chain or to aromatic sulphonic acid. More preferably formic acid, acetic acid, oxalic acid or p-toluene sulphonic acid are used. Examples of carboxylic acids from which component (a) also may be derived are dicarboxylic acids such as malonic acid, dimethylmalonic acid, succinic acid, glutaric acid, adipic acid, pimelic acid, suberic acid, azelaic acid, phthalic acid, isophthalic acid and terephthalic acid. The carboxylic acids from which component (a) may be derived may contain substituents, for example alkoxy groups, particularly those having not more than five carbon atoms, hydroxy groups, cyano groups and fluorine, chlorine, bromine and iodine atoms. Examples of such carboxylic acids are glycolic acid, 2-hydroxypropionic acid, 3-hydroxypropionic acid, glyceric acid, tartronic acid, malic acid, tartaric acid, tropic acid, benzilic acid, salicylic acid, anisic acid, gallic acid, 3,5-dichlorobenzoic acid, 3,5-dibromobenzoic acid, cyanoacetic acid, monofluroacetic acid, difluoroacetic acid, trifluoroacetic acid and trichloroacetic acid. Other examples of suitable acids from which component (a) may be derived are propanoic acid, butanoic acid, 2-methylpropanoic acid, pentanoic acid, 3-methylbutanoic acid, 2,2-dimethylpropanoic acid, hexanoic acid, heptanoic acid and octanoic acid, hydrochloric acid, sulphuric acid, nitric acid, phosphoric acid, methyl sulphonic acid and trifluoromethyl sulphonic acid. Further, compounds as copper acetylacetonate may also be used.

A mixture of the salts in question may be used in component (a), for example formate and oxalate, formate and acetate, or acetate and oxalate.

The salts in component (a) may contain crystal water, but are preferably free therefrom.

The alcohol of component (b) may be aromatic or cycloaliphatic but is preferably aliphatic. Preference is given to alkanols, in particular to those having in the range of from 1 to 20 carbon atoms per molecule. Among the latter alkanols those having of from 4 to 12 carbon atoms per molecule are preferred, because such alkanols can be easily separated from methanol by means of distillation. Examples of such alkanols are tert-butyl alcohol, tert-pentyl alcohol, hexanol, heptanol and alkanols having of from 8 to 12 carbon atoms per molecule. Tert-butyl alcohol and tert-pentyl alcohol are particularly preferred. Dihydric alcohols may also be used, for example ethylene glycol, propylene glycol, 1,3-dihydroxypropane, 1,2-butanediol, 1,3-butanediol, 1,4-butanediol, 2,3-butanediol or 1,2-pentanediol. Component (b) may also be glycerol.

Component (b) may be a mixture of alcohols, for example of tert-butyl alcohol and ethylene glycol or of tert-pentyl alcohol and 1,4-butanediol.

Component (c) may be a complex hydride derived from an alkali metal and a metal of Group III of the Periodic Table. The alkali metal is suitably chosen from lithium, sodium and potassium. The Group III metal is suitably chosen from boron and aluminium. Preferred complex hydrides are $LiAlH_4$, $NaAlH_4$, $KAlH_4$, $LiBH_4$, $NaBH_4$ and $KBH_4$. More preferably borohydrides are used, especially sodium borohydride. Further, complex hydrides containing one or more alkyl, alkoxy, aryloxy or cyano groups may be used. Suitable compounds in this respect are $LiBEt_3H$, $NaAlEt_2H_2$, $LiAlH(OMe)_3$, $LiAlH_3(O\text{-}tBu)$, $LiAL(Et_3CO)_3H$, $NaB(OAc)_3H$, and $NaBH_3CN$. Other suitable complex hydrides, e.g. $NaBH_2S_3$, may also be used. Mixtures of two or more complex hydrides are also included.

If desired, an alcoholate of an alkali metal or an alcoholate of an alkaline earth metal may also be combined in the catalytic system. This alcoholate is preferably a lithium, sodium or a potassium alcoholate. Among the alcoholates preference is given to sodium and potassium alkoxides, particularly to those having of from 1 to 20 carbon atoms per molecule, more particularly of from 1 to 6 carbon atom per molecule, such as sodium methoxide, sodium ethoxide, sodium propoxide, sodium butoxide, sodium isobutoxide, sodium tert-pentoxide, potassium tert-butoxide and potassium 2-methyldode-2-oxide.

The combination and reaction of components (a), (b) and (c) in the process according to the present invention may be carried out at a temperature which is not critical and may vary within wide ranges. The combination and reaction can be carried out at relatively low temperature, preferably in the range of from 0° C. to 100° C. Very good results are usually obtained at temperatures in the range of from 30° C. to 60° C.

It has, furthermore, been found that the activity of the catalytic system can be further enhanced by a pre-treatment. According to a preferred embodiment of the present invention the catalytic system is pre-treated by contacting it for a prolonged time with a gaseous mixture comprising carbon monoxide and hydrogen at such an elevated temperature and elevated pressure that no substantial consumption of carbon monoxide and hydrogen takes place. Usually, a period of from 10 min to 5 h at a temperature between 30° C. and 120° C., preferably between 50° C. and 90° C., and a pressure between 5 and 100 bar is sufficient for the pre-treatment. The pre-treatment has reached its end where the pressure progressively starts decreasing which is a signal for formation of substantial amounts of methanol. Surprisingly, the present pre-treatment consumes very little carbon monoxide and hydrogen but yet results in the formation of a catalytic system having a considerably enhanced activity for the production of methanol. At the end of the pre-treatment the temperature may be adjusted to the required reaction temperature, which is a value at which substantial amounts of methanol are produced. This adjustment may be an increase of the temperature, but it is also possible that the temperature can be decreased. Such an increase or decrease of the temperature will usually be over a range of 10° C. to 50° C. It is, however, possible, that no adjustment of the temperature is required at all, pre-treatment and methanol production being carried out at substantially the same temperature.

The process according to the present invention may be carried out at a temperature and a pressure which are not critical and may vary within wide ranges. Preferably, a temperature of from 60° C. to 150° C., more preferably of from 80° to 120° C. and a pressure of from 5 to 100 bar, more preferably of from 20 to 80 bar, still more preferably of from 30-60 bar are used.

The process according to the present invention may be carried out with an organic diluent in which the catalytic system is present, at least partly, as a suspension. Suitably, a weight ratio of organic diluent to component (a) of from 0.1 to 5000 is used, but this weight ratio may be lower than 0.1 or higher than 5000. Any inert diluent may in principle be used. Examples of suitable diluents are ketones, such as acetone, methyl ethyl ketone, methyl isobutyl ketone, acetophenone, cyclohexanone and acetylacetone; ethers such as anisole, 2,5,8-trioxanonane (also referred to as "diglyme"), diethyl ether, diphenyl ether, diisopropyl ether and tetrahydrofuran; aromatic hydrocarbons, such as benzene, toluene, the three xylenes and ethylbenzene; halogenated aromatic compounds, such as chlorobenzene and o-dichlorobenzen; halogenated alkanes, such as dichloromethane and carbontetrachloride; alkanes, such as hexane, heptane, octane, 2,2,3-trimethylpentane and kerosene fractions; cycloalkanes, such as cyclohexane and methylcyclohexane; nitriles, such as benzonitrile and acetonitrile; sulphoxides, such as dimethyl sulphoxide; sulphones, such as diisopropyl sulphone, tetrahydrothiophene-1,1-dioxide (also referred to as "sulfolane"), 2-methyl-4-butylsulfolane and 3-methylsulfolane. Mixtures of two or more solvents may be used. Very good results have been obtained with ethers.

The process according to the present invention is preferably carried out using a molar ratio of component (b) to component (a) of from 0.5:1 to 100:1 and, more preferably, from 1:1 to 50:1, still more preferably from 2:1 to 25:1, but the use of molar ratios below 0.5 and above 100 is not excluded. The process may be carried out using a molar ratio of component (c) to component (a) of from 0.1 to 1 to 100 to 1, preferably of from 1 to 1 to 10 to 1, more preferably of from 2 to 1 to 5 to 1.

In a preferred embodiment the process of the present invention is carried out in the presence of a certain amount of a basic nitrogen compounds. Preferred basic nitrogen compounds are aromatic nitrogen compounds in which the nitrogen atom forms a part of the aromatic system, e.g. pyridine, quinoline etc. Especially preferred is pyridine. Suitably, a molar ratio of basic nitrogen compound to component (a) of from 0.5 to 1 to 50 to 1 is used, preferably 1 to 1 to 10 to 1.

The carbon monoxide and hydrogen may be used as pure gases or diluted with an inert gas such as a noble gas or nitrogen. The process according to the present invention may be carried out using a molar ratio carbon monoxide to hydrogen in the gaseous mixture which is not critical and may vary within wide ranges, suitably of from 1:0.2 to 1:20. The carbon monoxide and hydrogen may be obtained by partial oxidation of hydrocarbons, for example of natural gas.

The methanol produced according to the invention forms another feature of the invention. It may be used for a variety of purposes, for example for the manufacture of synthetic gasoline, as a fuel component and for the production of methyl tert-butyl ether.

The process according to the present invention may be carried out batchwise, semi-continuously or continuously.

The invention also relates to a novel composition obtainable by combination of:

component (a): a copper salt,
component (b): an alcohol, and
component (c): a complex hydride, and
allowing the combined components to react.

Said novel composition may be used as a catalytic system in the process according to the present invention.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described the the following examples which are provided for illustration purposes and are not to be construed as limiting the invention.

Each experiment was carried out in a 300 ml Hastelloy C autoclave (Hastelloy is a trade mark) provided with a magnetic stirrer. The reaction mixtures were analyzed by means of gas-liquid chromatography.

EXAMPLE 1

The autoclave was charged under a nitrogen atmosphere with diglyme (50 ml), copper acetate (5 mmol), sodium borohydride (20 mmol) and methanol (10 ml, 8 g), heated to a temperature of 50° C. and stirred for 1 hour. Potassium t-butanolate (60 mmol) was added, the autoclave was sealed and a mixture of 1 volume of carbon monoxide and 2 volumes of hydrogen was added until a pressure of 45 bar was obtained.

The autoclave was heated for 5 hours at 100° C. while keeping the pressure between 30 and 60 bar (average 45 bar) by intermittently introducing said mixture of carbon monoxide and hydrogen. A water-white solution was obtained containing 11 grams of methanol (3 grams formed).

EXAMPLE 2

Example 1 was repeated using 10 mmol copper acetate instead of 5 mmol. Yield: 4 grams of methanol were formed.

Comparative Example A

Example 2 was repeated, however, no methanol was used. Yield: 0.6 g of methanol.

EXAMPLE 3

Example 1 was repeated using pentanol (50 ml) instead of diglyme as solvent. No methanol was used. Yield. 6.0 g of methanol.

EXAMPLE 4

Example 1 was repeated using pentanol (50 ml) instead of diglyme as solvent. Pyridine (10 mmol) was added to the reaction mixture. No methanol was used. The reactor temperature was 80° C. Yield: 4.0 g of methanol.

We claim:

1. A process for the preparation of methanol comprising contacting at a temperature of about 60° C.–150° C. and a pressure of about 5–100 bar a gaseous mixture comprising carbon monoxide and hydrogen with a catalytic system obtained by combining the following components:

Component (a): a copper salt of a carboxylic acid or a sulphonic acid,
Component (b): an alkanol having from 1 to 20 carbon atoms per molecule, and
Component (c): a complex hydride derived from an alkali metal selected from lithium, sodium, potassium and mixtures thereof and a Group III metal selected from boron, aluminum and mixtures thereof.

2. The process as claimed in claim 1 in which the carboxylic acid is an alkanoic acid having 1–10 carbon atoms in the chain.

3. The process as claimed in claim 2 in which the alkanoic acid is acetic acid.

4. The process as claimed in claim 1 in which the alkanol has from 4 to 12 carbon atoms per molecule.

5. The process as claimed in claim 4 in which the alkanol is pentanol.

6. The process as claimed in claim 1 in which the alkali metal is sodium.

7. The process as claimed in claim 1 in which the Group III metal is boron.

8. The process as claimed in claim 1 in which the complex hydride is sodium borohydride.

9. The process as claimed in claim 1 in which the catalytic system is pre-treated by contacting it for a prolonged time with a gaseous mixture comprising carbon monoxide and hydrogen at such an elevated temperature and pressure that no substantial consumption of carbon monoxide and hydrogen takes place.

10. The process as claimed in claim 1 in which a temperature of 80° C. to 120° C. and a pressure from 20 to 80 bar are used.

11. The process as claimed in claim 1 in which a basic nitrogen compound is present during the reaction.

12. The process as claimed in claim 11 in which the basic nitrogen compound is pyridine.

* * * * *